United States Patent
Mohl

(10) Patent No.: US 8,996,106 B2
(45) Date of Patent: *Mar. 31, 2015

(54) METHOD AND DEVICE FOR INTERMITTENT OCCLUSION OF A VEIN DRAINING THE ORGAN SYSTEM

(71) Applicant: Miracor Medical Systems GmbH, Vienna (AT)

(72) Inventor: Werner Mohl, Altenmarkt-Thennenberg (AT)

(73) Assignee: Miracor Medical Systems GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/959,176

(22) Filed: Aug. 5, 2013

(65) Prior Publication Data

US 2013/0317284 A1 Nov. 28, 2013

Related U.S. Application Data

(63) Continuation of application No. 13/437,325, filed on Apr. 2, 2012, now Pat. No. 8,500,623, which is a continuation of application No. 12/312,794, filed as application No. PCT/AT2007/000543 on Nov. 30, 2007, now Pat. No. 8,162,813.

(30) Foreign Application Priority Data

Nov. 30, 2006 (AT) .................................. A19992006

(51) Int. Cl.
*A61M 1/10* (2006.01)
*A61B 17/12* (2006.01)
(Continued)

(52) U.S. Cl.
CPC .............. *A61M 1/1072* (2013.01); *A61B 17/12* (2013.01); *A61M 25/1018* (2013.01);
(Continued)

(58) Field of Classification Search
CPC ............ A61M 25/10; A61M 25/1011; A61M 25/1018; A61M 1/1072; A61M 1/3613; A61M 2025/1095; A61M 2025/1097

USPC .............. 600/485, 486, 488, 16–18; 606/158; 623/3.1

See application file for complete search history.

(56) References Cited

U.S. PATENT DOCUMENTS

| | | | |
|---|---|---|---|
| 4,459,977 A | 7/1984 | Pizon et al. | |
| 4,493,697 A * | 1/1985 | Krause et al. | 604/522 |

(Continued)

FOREIGN PATENT DOCUMENTS

| | | |
|---|---|---|
| DE | 195 14 638 | 10/1996 |
| DE | 195 26 784 | 1/1997 |

(Continued)

OTHER PUBLICATIONS

Mohl et al., "Intermittent pressure elevation of the coronary venous system as a method to protect ischemic myocardium," *Interact CardioVac Thorac Surg.*, 2005, 4:66-69.

(Continued)

*Primary Examiner* — Carl H Layno
*Assistant Examiner* — Eugene Wu
(74) *Attorney, Agent, or Firm* — Fish & Richardson P.C.

(57) ABSTRACT

In a method for the intermittent occlusion of a vein draining the organ system, in which the vein is occluded by an occlusion device, the fluid pressure in the occluded vein is continuously measured and stored, the behavior of the fluid pressure is determined as a function of time, and the occlusion of the vein is triggered and/or released as a function of at least one characteristic value derived from the pressure measurements, pressure is applied during the occlusion in a pulsating manner. The device for the intermittent occlusion of a vein, including an occlusion device, a pressure measuring device for continuously measuring the fluid pressure in the occluded vein, and a memory for storing the fluid pressure behavior as a function of time, means are provided for applying a pulsating pressure in the occluded vein.

15 Claims, 2 Drawing Sheets

(51) Int. Cl.
    *A61M 25/10* (2013.01)
    *A61M 1/36* (2006.01)
    *A61B 5/0215* (2006.01)
    *A61B 17/00* (2006.01)
    *A61M 25/00* (2006.01)

(52) U.S. Cl.
    CPC .......... *A61M 1/1086* (2013.01); *A61M 1/3613* (2013.01); *A61B 5/02152* (2013.01); *A61B 2017/00557* (2013.01); *A61M 2025/0002* (2013.01); *A61M 2025/1052* (2013.01); *A61M 2205/3344* (2013.01)
    USPC ............................................. 607/17; 600/486

(56) References Cited

U.S. PATENT DOCUMENTS

| | | |
|---|---|---|
| 4,969,470 A | 11/1990 | Mohl et al. |
| 5,011,468 A | 4/1991 | Lundquist et al. |
| 5,024,668 A | 6/1991 | Peters et al. |
| 5,033,998 A | 7/1991 | Corday et al. |
| 6,458,323 B1 | 10/2002 | Boekstegers |
| 6,755,821 B1 | 6/2004 | Fry |
| 7,083,588 B1 | 8/2006 | Shmulewitz et al. |
| 7,331,922 B2 | 2/2008 | Mohl |
| 8,162,813 B2 | 4/2012 | Mohl |
| 8,500,623 B2 | 8/2013 | Mohl |
| 2002/0091349 A1 | 7/2002 | Reich |
| 2003/0100911 A1 | 5/2003 | Nash et al. |
| 2004/0098030 A1 | 5/2004 | Makower et al. |
| 2004/0172004 A1* | 9/2004 | Mohl ............................ 604/509 |
| 2004/0220522 A1 | 11/2004 | Briscoe et al. |
| 2005/0059930 A1 | 3/2005 | Garrison et al. |
| 2005/0113799 A1 | 5/2005 | Lenker |
| 2006/0100550 A1 | 5/2006 | Schultheiss et al. |
| 2006/0173298 A1 | 8/2006 | Tucker |
| 2006/0246044 A1 | 11/2006 | Lutz et al. |
| 2006/0258980 A1 | 11/2006 | Bridges et al. |
| 2007/0203445 A1 | 8/2007 | Kaye et al. |

FOREIGN PATENT DOCUMENTS

| | | |
|---|---|---|
| EP | 0 230 996 | 8/1987 |
| EP | 1 188 417 | 3/2002 |
| WO | WO 00/33913 | 6/2000 |
| WO | WO 02/05887 | 1/2002 |
| WO | WO 03/008018 | 1/2003 |

OTHER PUBLICATIONS

Mohl, Werner et al. "Coronary Sinus Library, ICSO and PICSO" Society of Coronary Sinus Interventions, 2003. A. Holzhausens Nfg., Austria.

Syeda et al., "The salvage potential of coronary sinus interventions: Meta-analysis and pathophysiologic consequences," *J Thorac Cardiovasc Surg.*, 2004, 124:1703-1712.

* cited by examiner

METHOD AND DEVICE FOR INTERMITTENT OCCLUSION OF A VEIN DRAINING THE ORGAN SYSTEM

CROSS-REFERENCE TO RELATED APPLICATIONS

This is a continuation of U.S. application Ser. No. 13/437,325 filed on Apr. 2, 2012, now U.S. Pat. No. 8,500,623,which is a continuation of U.S. application Ser. No. 12/312,794 filed on May 27, 2009, now U.S. Pat. No. 8,162,813,which is a National Stage application under 35 U.S.C. §371 and claims benefit under 35 U.S.C. §119(a) of International Application No. PCT/AT2007/000543 filed on Nov. 30, 2007, which claims the benefit of Austrian Application Serial No. A1999/2006 filed on Nov. 30, 2006, and all of these aforementioned disclosures are incorporated by reference in their entirety into this application.

TECHNICAL FIELD

The invention relates to a method for the intermittent occlusion of a vein draining the organ system, in which the vein is occluded by an occlusion device, the fluid pressure in the occluded vein is continuously measured and stored, the behavior of the fluid pressure is determined as a function of time, and the occlusion of the vein is triggered and/or released as a function of at least one characteristic value derived from the pressure measurements, and to a device for carrying out said method. The veins concerned, for instance, include the jugular vein and the coronary sinus.

BACKGROUND

Arterial blood, which supplies the heart muscle, is able to pass through healthy heart tissue while nourishing the same, yet has difficulty reaching ischemic tissue. As a result, the supply of ischemic tissue with nutrients and the discharge of metabolic catabolites from such ischemic tissue will be impaired.

In this context, it has already been proposed to supply the ischemic tissue with blood through retrograde perfusion. In doing so, attempts have been made to allow the blood to flow back from the coronary sinus through the coronary venous system in counterflow by feeding blood from a different source into the coronary sinus, either by permanently connecting an artery with the coronary sinus or by temporarily inserting a catheter into the sinus, which catheter is supplied with blood taken from a remote artery and transported by the aid of a blood pump located outside the patient's body.

The initially proposed technique for retroperfusion uses an inflatable balloon fixed to the end of a catheter to intermittently occlude the coronary sinus. The blood pressure in the coronary sinus rises during the occlusion at every heart beat so as to cause blood reaching the coronary sinus through the healthy tissue of the heart muscle to be flushed back into the ischemic tissue. For such an intermittent coronary sinus occlusion, the balloon end of the catheter is inserted either percutaneously or surgically. The other end of the catheter is supplied with a gas or fluid by a pump which causes the cyclic inflation and deflation of the balloon.

A typical application of blood retroinfusion in coronary veins by the intermittent occlusion of the coronary sinus applies to myocardial protection during a short-term coronary arterial occlusion in the context of a cardiologic intervention. A typical such intervention, for instance, includes the balloon dilatation of an arteriosclerotically constricted coronary artery. That method, which is also known as percutaneous transluminal coronary angioplasty (PTCA), comprises the conduction of a balloon catheter into the region of the coronary artery stenosis under X-ray control and the compression of the arteriosclerotic plaque by the inflation of the balloon located on the end of the catheter. During the dilatation of the balloon, no supply of the tissue with oxygen-containing blood takes place downstream in the artery, with functional changes in the ischemic area of the myocard being detectable already at dilatations lasting longer than 30 seconds. Problems involved in the ischemic protection of the myocard will also be faced in other interventions aimed at coronary vascularization such as, e.g., atherectomy, coronary endoprostheses, laser applications and percutaneous surgeries of the cardiac valves.

A device for the retroinfusion of coronary veins has, for instance, become known from EP 230 996 A2, by which a pressure-controlled intermittent coronary sinus occlusion can be performed. The device comprises a means for occluding the sinus such as, e.g., an inflatable balloon catheter, a pressure measuring unit for measuring the fluid pressure within the coronary sinus and a control unit which generates triggering signals for the occlusion device to trigger or release an occlusion. The control unit is devised in a manner that the pressure maximum in the coronary sinus is measured during every heart beat, a plateau value of the pressure maxima of consecutive heart beats is estimated by calculation and the occlusion of the coronary sinus is released on the basis of the plateau value of the pressure maxima.

The occlusion of the coronary sinus causes a pressure increase and, subsequently, a retroperfusion of blood via the respective vein into the nutritive capillaries of the ischemic area so as to enable the supply of nutrients to that area. At a release of the occlusion, the retroperfused blood is flushed out while the metabolic waste products are carried off at the same time.

In a series of investigations, it could be demonstrated that endothelial growth factors inter alia respond to the application of mechanical loads and, in particular, pressure. While the blood is passing through the vessels, the endothelium basically is acted upon not only by shearing forces but, naturally, also by the initially mentioned pressures, whereby a pressure increase lasting for as long as possible will, in principle, lead to an increased release of vessel-forming genes (VEGF genes, vascular endothelial growth factor encoding genes), which will be beneficial to the regeneration of the heart vessels and, in particular, neoangiogenesis. It is, however, not possible to achieve an indefinitely long lasting pressure increase by an occlusion using known methods, since the occlusion must again be intermittently released after having reached the plateau value, thus causing the pressure to be lowered again.

SUMMARY

The invention now aims to enhance the contribution to neoangiogenesis based on a pressure increase or changing pressure sensitivity and to improve these effects theoretically recognized as positive. To solve this object, the method according to the invention, departing from the initially described method, essentially consists in that pressure is applied during the occlusion in a pulsating manner. It could be experimentally demonstrated that a linear pressure increase as well as the mere shearing stress of the endothelium contribute considerably less to the production of vascular endothelial growth factors, and hence to neoangiogenesis. It is only by the pulsating application of pressure proposed by the invention that this effect will be improved, wherein it is essential in this connection that said pulsating pressure be applied during the occlusion and, hence in the phase in which a pressure build-up is generally effected until the achievement of a plateau value. In a particularly advantageous manner, the method according to the invention is carried out in that the pulsating pressure build-up is applied pneumatically or hydraulically via an oscillating, pulsating membrane, in particular a further balloon, or piezoelectrically, whereby pressure waves at frequencies of between 50 and 250 per minute and, in particular, 100 to 200 per minute are introduced. In principle, the frequency of these pressure waves preferably is to be chosen higher than what would correspond to the pulse rate of a grownup human. The relatively high pulse rates of 100 to 200 per minute largely correspond to pulse rates as are observed in newborns and, in particular, during the development phase of the heart. Such pulse rates have turned out to be of particular advantage for angioneogenesis. In a particularly advantageous manner, the method is carried out such that the pressure wave maxima are synchronized with ECG signals, heart tones and/or phasic temperature changes in the blood flow.

The device according to the invention for the intermittent occlusion of a vein, including an occlusion device, a pressure measuring device for continuously measuring the fluid pressure in the occluded vein, and a memory for storing the fluid pressure behavior as a function of time, is essentially characterized in that means are provided for applying a pulsating pressure in the occluded vein. A device of this type is suitable for carrying out the method according to the invention, the means for applying said pulsating pressure being, as a rule, arranged in the occluded portion of the vein distally of the occlusion device.

In a preferred manner, the means for applying a pulsating pressure are comprised of an oscillating body, said oscillating body being drivable to form pressure waves. Such an oscillating body is able to induce the formation of pressure waves according to different principles, said oscillating body in a preferred manner being arranged in a cage designed in the manner of a stent. The cage preferably provided in connection with said device, in the manner of a stent provides security to the region in which the oscillating body is to enter into effect, thus preventing a direct collision of the oscillating body with the vessel wall. In this manner, the desired pulsating pressure waves can be efficiently built up with little mechanical expenditure, the pressure build-up being basically achievable by various mechanical converters. In this respect, a configuration in which the oscillating body is comprised of a pneumatically or hydraulically expandable hollow body or balloon is particularly preferred.

In order to ensure that the higher-frequency pulsations also result in accordingly elevated pressure peak values, with the stimulation of the endothelium thus being effected in the desired manner, the configuration is advantageously devised such that the oscillating body is coupled with the occlusion device and additionally drivable to pulsations during the time of the occlusion-related pressure build-up.

With the initially mentioned device, a pressure measuring device is basically employed in such a manner that, after having estimated the respective plateau value occurring as a result of an occlusion, the appropriate relief of the balloon is also effected and the occlusion is released again. This measurement is, however, irrelevant to the actual success of the pulsating pressure such that appropriate control is not readily feasible. The configuration is, therefore, advantageously devised such that the pressure measuring device is designed to measure the fluid pressure in the occluded coronary sinus and to measure the pressure peaks introduced by the oscillating body.

In a preferred manner, the configuration is devised such that the means for applying a pulsating pressure is comprised of a device for the pulsating introduction of perfusate into the occluded vein. Such a configuration not only enables the generation of the desired pressure waves, but in addition renders feasible the use of, for instance, fresh blood for nourishing the ischemic tissue, whereby even blood lost from the bloodstream at another location during an intervention can be compensated for.

In a particularly advantageous manner, the device according to the invention is further developed such that a device controlling the formation of said pressure waves is arranged to generate pressure waves from a lower threshold value of the detectable pressure increase after the occlusion and to stop the generation of pressure waves upon release of the occlusion. To synchronize the pressure wave maxima with relevant parameters for the circulatory function, the configuration is preferably devised such that a device controlling the formation of said pressure waves is connectable with signal lines for ECG signals, heart tones and/or temperature measurements.

The device according to the invention is advantageously further developed to the effect that the formation of said pressure waves is inducible as a function of the blood pressure peaks produced by the heart. The formation of pressure waves can thus be synchronized with the occurrence of blood pressure peaks so as to enable the retrograde perfusion of the ischemic tissue in a particularly effective manner with little expenditure.

In a preferred manner, the formation of pressure waves is inducible by a fluid pulsingly conveyed within the lumen. Such a pneumatically driven configuration is characterized by a simple handling and a particularly direct response characteristic. In a preferred manner, the formation of said pressure waves can, moreover, be induced by sonic waves and, in particular, ultrasonic waves, as well as by electromechanical and, in particular, nanoelectromechanical waves, as in correspondence with a preferred embodiment of the device according to the invention. In this manner, pressure waves of virtually any frequency can be generated.

According to a preferred embodiment, the device according to the invention is further developed to the effect that the formation of said pressure waves is inducible by a combination of the action of the occlusion device and the action of the means for applying a pulsating pressure in the vein. In this manner, the occlusion device can be used to generate pressure waves in addition to the means for applying a pulsating pressure, thus enabling the formation of especially strong pressure waves.

DESCRIPTION OF DRAWINGS

In the following, the invention will be explained in more detail by way of an exemplary embodiment illustrated in the drawing.

Therein.

DETAILED DESCRIPTION

Figure 1:
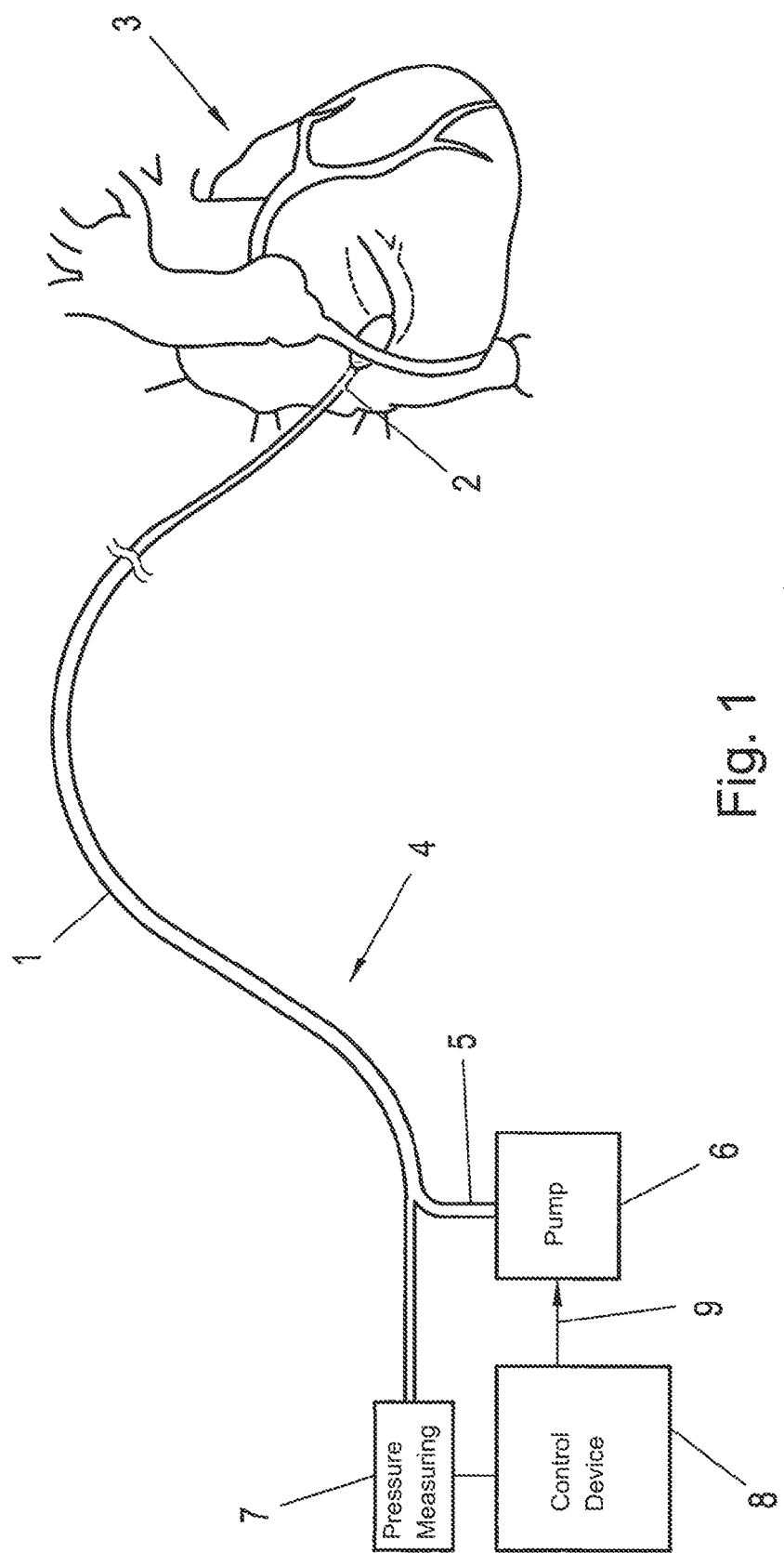
FIG. 1 is a diagrammatic view of a heart with a device for the intermittent occlusion of the coronary sinus.

FIG. 1 schematically depicts the device for the intermittent occlusion of the coronary sinus, wherein a multi-lumen catheter 1 is shown, whose distal end 2 is inserted in the coronary sinus of the heart 3 via the atrium. The proximal end 4 of the catheter 1 has a balloon inflation lumen 5 connected with a pump 6. The pressure prevailing on the distal end 2 of the catheter 1 is detected by a pressure measuring device 7, the latter also including a memory for the measured values acquired. The respectively measured pressure values are fed to a control device 8 including a calculation unit, which delivers control signals via line 9 for starting and stopping the pump 6.

Figure 2:
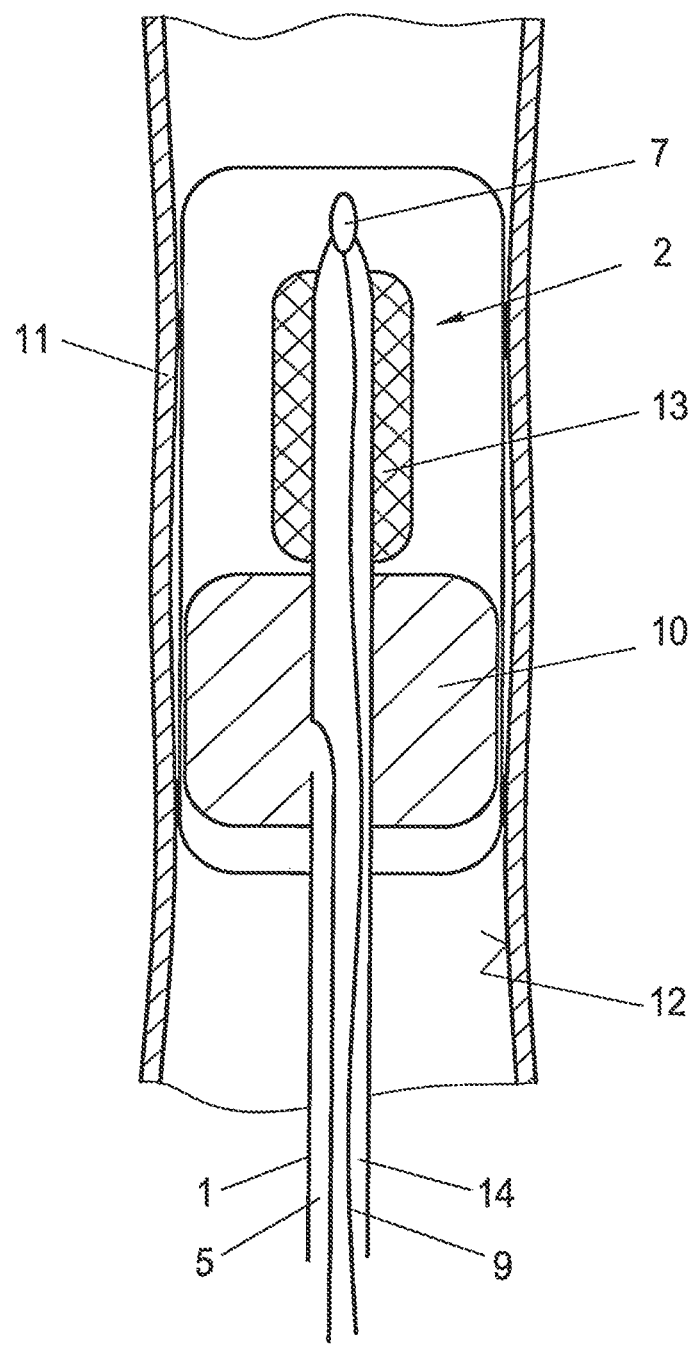
FIG. 2 is an enlarged illustration of the distal end of the catheter according to the invention.

FIG. 2 illustrates the distal end 2 of the multi-lumen catheter 1 on an enlarged scale. The balloon inflation lumen in this case runs into the balloon 10, which is shown in FIG. 2 in the expanded and hence occluding position. The distal end is secured by a stent-like cage 11, which can be pressed onto the vessel wall 12 so as to avoid any direct collision of said end with the aorta or vessel wall. The distal end, besides the balloon 10, now also carries a vibrator body 13, to which hydraulic pressure pulses can be fed, for instance through lumen 14. During the occlusion, i.e. with the balloon 10 inflated, pressure medium is thus pulsingly introduced into the vibrator body 13 via lumen 14 so as to obtain the respective pressure change load by the thus enhanced stimulation of the factors triggering neoangiogenesis.

What is claimed is:

1. A method for intermittent occlusion of a coronary sinus, comprising the steps of:
    occluding a coronary sinus of a patient using an occlusion device coupled to a distal end portion of the multi-lumen catheter and being in communication with a first lumen of the multi-lumen catheter, the occlusion device being adjustable between a non-occluding state and an occluding state that is configured to substantially occlude the coronary sinus;
    measuring and storing fluid pressure values in the occluded coronary sinus during said occluding step;
    during said occluding step, outputting a pulsating pressure into the occluded coronary sinus from the distal end portion of the multi-lumen catheter positioned in the coronary sinus, wherein the pulsating pressure is output into the coronary sinus using pressure waves at a frequency greater than a pulse rate of the patient, wherein said outputting the pulsating pressure into the occluded coronary sinus comprise outputting the pulsating pressure from a pulsating device attached to the distal end portion of the multi-lumen catheter and positioned in the coronary sinus, wherein said pulsating device comprises a pulsating membrane structure in communication with a second lumen of the multi-lumen catheter, the pulsating membrane structure being positioned at least partially distal of the occlusion device; and
    releasing the occlusion of the coronary sinus as a function of at least one characteristic value derived from said pressure values in the occluded coronary sinus.

2. The method of claim 1, wherein said outputting the pulsating pressure occurs only during the occlusion of the coronary sinus when the occlusion device is in the occluding state.

3. The method of claim 1, wherein said outputting the pulsating pressure comprises applying the pulsating pressure pneumatically or hydraulically into an interior space defined by the pulsating membrane structure.

4. The method of claim 1, wherein said outputting the pulsating pressure into the occluded coronary sinus comprises outputting pressure waves into the occluded coronary sinus at a frequency between 50 and 250 per minute.

5. The method of claim 1, wherein said outputting the pulsating pressure into the occluded coronary sinus initiates at a lower threshold value of a detectable pressure increase after the occlusion and then stops upon release of the occlusion.

6. The method of claim 1, wherein said releasing the occlusion of the coronary sinus includes adjusting the occlusion device from the occluded state to the non-occluding state.

7. A method for intermittent occlusion of a coronary sinus, comprising the steps of:
    occluding a coronary sinus of a patient using an occlusion device coupled to a distal end portion of the multi-lumen catheter and being in communication with a first lumen of the multi-lumen catheter, the occlusion device being adjustable between a non-occluding state and an occluding state that is configured to substantially occlude the coronary sinus;
    measuring and storing fluid pressure values in the occluded coronary sinus during said occluding step;
    during said occluding step, outputting a pulsating pressure into the occluded coronary sinus from a pulsating membrane structure coupled to the distal end portion of the multi-lumen catheter and positioned in the coronary sinus, wherein the pulsating membrane structure outputs pressure waves at a frequency greater than a pulse rate of the patient,
    releasing the occlusion of the coronary sinus as a function of at least one characteristic value derived from said pressure values in the occluded coronary sinus.

8. The method of claim 7, wherein said outputting the pulsating pressure into the occluded coronary sinus comprises applying the pulsating pressure pneumatically or hydraulically to the pulsating membrane structure.

9. The method of claim 8, said outputting the pulsating pressure into the occluded coronary sinus comprises the pulsating membrane structure outputting pressure waves at the frequency between 50 and 250 per minute.

10. The method of claim 7, wherein said pulsating membrane comprises a distal balloon structure in communication with a second lumen of the multi-lumen catheter, the distal balloon structure being positioned at least partially distal of the occlusion device.

11. The method of claim 10, wherein said outputting the pulsating pressure comprises applying the pulsating pressure pneumatically or hydraulically into an interior space of the distal balloon structure.

12. The method of claim 7, wherein the pulsating membrane structure is positioned the distal end portion of the multi-lumen catheter at least partially distal of the occlusion device.

13. The method of claim 12, wherein said releasing the occlusion of the coronary sinus includes adjusting the occlusion device from the occluded state to the non-occluding state.

14. The method of claim 7, wherein said outputting the pulsating pressure occurs only during the occlusion of the coronary sinus when the occlusion device is in the occluding state.

15. The method of claim 7, wherein said outputting the pulsating pressure into the occluded coronary sinus initiates at a lower threshold value of a detectable pressure increase after the occlusion and then stops upon release of the occlusion.

* * * * *